United States Patent
Anderson

(10) Patent No.: US 7,383,970 B2
(45) Date of Patent: *Jun. 10, 2008

(54) VALVE WITH A TWO-COMPONENT SEAL

(75) Inventor: Gregor John McLennan Anderson, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/198,253

(22) Filed: Aug. 5, 2005

(65) Prior Publication Data

US 2005/0269546 A1    Dec. 8, 2005

Related U.S. Application Data

(63) Continuation of application No. 10/049,129, filed as application No. PCT/EP00/06225 on Jul. 4, 2000, now Pat. No. 6,926,178.

(30) Foreign Application Priority Data

Aug. 7, 1999    (GB)    ................... 9918626.4

(51) Int. Cl.
    *B65D 83/00*    (2006.01)
(52) U.S. Cl. ............... 222/402.2; 222/402.24; 277/562
(58) Field of Classification Search ........ 222/402.1, 222/402.2, 402.22, 402.23, 402.24, 162, 222/635, 542; 239/337; 277/945, 568, 562
    See application file for complete search history.

(56) References Cited

U.S. PATENT DOCUMENTS

| 3,104,785 A | 9/1963 | Beard, Jr. | |
| 3,158,179 A | 11/1964 | Lehmann | |
| 3,394,851 A | 7/1968 | Gorman | |
| 3,640,436 A | 2/1972 | Gallagher | |
| 3,705,667 A * | 12/1972 | Blanie et al. | 222/136 |
| 3,900,139 A | 8/1975 | Myers | |
| 3,933,206 A | 1/1976 | Burke | |
| 4,548,338 A | 10/1985 | Sander | |
| 4,744,495 A | 5/1988 | Warby | |
| 4,819,834 A | 4/1989 | Thiel | |
| 4,919,312 A | 4/1990 | Beard et al. | |
| 4,936,492 A * | 6/1990 | Amiel et al. | 222/207 |
| 4,944,433 A | 7/1990 | Knecht et al. | |
| 5,027,986 A | 7/1991 | Heinzel et al. | |
| 5,037,012 A | 8/1991 | Langford | |
| 5,037,013 A * | 8/1991 | Howlett | 222/402.2 |
| 5,183,189 A | 2/1993 | Baudin | |
| 5,484,088 A * | 1/1996 | Martin | 222/402.2 |
| 5,836,299 A | 11/1998 | Kwon | |
| 5,927,563 A | 7/1999 | Kellner | |
| 6,032,835 A * | 3/2000 | Burt | 222/402.1 |
| 6,129,905 A | 10/2000 | Cutie | |

(Continued)

FOREIGN PATENT DOCUMENTS

DE    4011653    10/1991

(Continued)

*Primary Examiner*—Frederick C. Nicolas
(74) *Attorney, Agent, or Firm*—J. Michael Strickland

(57) ABSTRACT

A valve that includes a valve body, a valve stem having a dispensing passage, and a sealing ring that contacts the valve stem is described. The sealing ring includes a flexible component and a rigid component.

11 Claims, 4 Drawing Sheets

U.S. PATENT DOCUMENTS 6,153,173 A    11/2000  Sapsford et al.
6,926,178 B1 *  8/2005  Anderson ................ 222/402.2

FOREIGN PATENT DOCUMENTS

| | | |
|---|---|---|
| EP | 0870699 | 10/1998 |
| GB | 2209514 | 5/1989 |
| GB | 2298187 | 8/1996 |
| GB | 2307224 | 5/1997 |
| WO | 9856445 | 12/1998 |
| WO | 9906303 | 2/1999 |

* cited by examiner

VALVE WITH A TWO-COMPONENT SEAL

CROSS-REFERENCE TO RELATED APPLICATIONS

This application is a continuation application of pending U.S. patent application Ser. No. 10/049,129, filed Feb. 6, 2002, now U.S. Pat. No. 6,926,178 which application was filed pursuant to 35 U.S.C. 371 as a United States National Phase Application of International Application No. PCT/EP00/06225, filed July 4, 2000, which claims priority from GB 9918626.4, filed on August 7, 1999.

FIELD OF INVENTION

This invention relates to a valve for an aerosol container with the aid of which a quantity of the contents thereof can be dispensed. The invention has particular application to the dispensing of metered doses of medicaments, though it is applicable to the dispensing of aerosols generally.

BACKGROUND TO THE INVENTION

Containers for aerosol formulations commonly comprise a vial body coupled to a valve. The valve comprises a valve stem through which the formulation is dispensed. Generally the valve includes a rubber valve seal intended to allow reciprocal movement of the valve stem while preventing leakage of propellant from the container.

It has been found that in some conventional devices the valve stem may tend to stick, pause, or drag during the actuation cycle with the result that the user may perceive a 'notchiness' as the valve stem is depressed and released. This may be partly caused by the drug sedimenting or precipitating out of the drug-propellant suspension or solution formulation and depositing on the internal valve components, the presence of drug on the sliding interface creating increased friction during operation.

Prior art seals generally comprise a rubber ring formed by stamping out a ring shape from a sheet of rubber material. The ring aperture, thus, inevitably has square-cut edges which present a relatively high area of contact between the seal and the stem. Furthermore, when the valve stem is moved in such square-cut seals the seal deforms in such a way that the surface area, and hence the frictional contact area, between the seal and stem increases.

The Applicants have now found that the above described problem of notchiness may be ameliorated without compromising sealing performance if the valve seal consists of two components: a rigid component and a flexible component. The two components may be arranged so that there is a rigid outer section and a flexible inner section. The flexible section allows for movement of the seal against the stem, while the rigid outer section reduces deformation of the seal and therefore keeps the increase in surface area, and hence frictional contact area, to a minimum. The two components may also be arranged in other suitable ways.

The increase in surface area may be further reduced by shaping the seal so as to reduce the area of contact between the seal and the stem. Cutting one or more grooves or small channels in the non stem-receiving surfaces of the sealing ring provides space for the stem-receiving part of the sealing ring to move into upon movement of the valve stem, resulting in reduced deformation and friction at the contact surface with the valve stem.

A further problem with prior art seals arises due to ingress and absorption of propellant (e.g. HFA 134a) and moisture by the rubber seal. The presence of the propellant or moisture in the rubber can lead to swelling of the rubber material and consequently a reduction in the performance of the seal. The use of a two component valve seal can reduce the amount of swelling occurring if one component is composed of material more resistant to propellant and moisture, thereby decreasing the amount of propellant or moisture absorbing material present in the seal.

SUMMARY OF THE INVENTION

According to one aspect of the present invention there is provided a valve for an aerosol container, the valve comprising a valve body; a valve stem having a dispensing passage, and contacting said valve stem, a sealing ring; the valve stem being slidably movable relative to the sealing ring from a valve-closed position to a valve-open position in which the interior of the valve body is in communication with the dispensing passage, wherein the sealing ring comprises a flexible component and a rigid component.

Preferably the valve is a metering valve wherein the valve body has a metering chamber, a sampling chamber and therebetween is provided a second sealing ring within which the stem is slidably movable, the valve stem having a transfer passage such that in the valve-closed position the dispensing passage is isolated from the metering chamber and the metering chamber is in communication with the sampling chamber via said transfer passage, and in the valve-open position the dispensing passage is in communication with the metering chamber and the transfer passage is isolated from the metering chamber, wherein the second sealing ring is composed of a rigid component and a flexible component.

Preferably the flexible component has a Shore A value of 45 to 80. Preferably the rigid component has a Shore A value of greater than 80. The Shore A hardness value may be determined by forcing a truncated cone under known load onto the material under examination and measuring the resultant degree of penetration.

Preferably the rigid component has a greater resistance to propellant and/or moisture than the flexible component. That is to say, the rigid component has more resistance to the ingress of moisture and propellant, and therefore a reduced tendency to swelling, compared with the flexible component.

Preferably the sealing ring and/or second sealing ring consists of an outer rigid ring component and an inner flexible ring component. The inner and outer ring components are arranged concentrically with the inner component receiving the valve stem.

Alternatively the sealing ring and/or second sealing ring consists of a flexible component surrounding a rigid core component. The flexible component completely surrounds the rigid component and receives the valve stem. The rigid component does not have any contact with the valve stem.

In one aspect the stem receiving part of the sealing ring and/or second sealing ring has rounded edges. These rounded edges reduce the area of contact between the sealing ring and/or second sealing ring and the valve stem and further reduces the deformation of the seal.

In another aspect the stem receiving part of the sealing ring and/or second sealing ring presents a lobed surface to the stem. That is to say the surface comprises one or more lobe features. Preferably the lobed surface and the seal receiving part of the stem define one or more wells. More preferably, the one or more wells contain lubricant material therein.

In another aspect of the invention the stem receiving part of the sealing ring and/or second sealing ring presents a tapered surface to the stem.

Preferably the non stem-receiving part of the sealing ring includes a groove. The groove provides additional free space for the sealing ring to flex back into upon movement of the valve stem.

Preferably the stem receiving part of the sealing ring and/or second sealing ring includes serrations. Preferably the serrations contain lubricant.

A further improvement which can be made to reduce the amount of swelling is to include serrations in the stem-receiving part of the sealing ring and/or second sealing ring. These serrations can be filled with lubricant to improve the strength of the seal, therefore reducing the presence of moisture between the seal and the valve stem.

Preferably the rigid component of the sealing ring and/or second sealing ring is composed of a material selected from the group consisting of polybutylteraphthalate, polyoxymethylene, a metal and nylon. Suitable metals include stainless steel and aluminium.

Preferably the flexible component of the sealing ring and/or second sealing ring is composed of an elastomeric material.

The elastomeric material may either comprise a thermoplastic elastomer (TPE) or a thermoset elastomer which may optionally be cross-linked. The flexible component of the sealing ring and/or second sealing ring may also comprise a thermoplastic elastomer blend or alloy in which an elastomeric material is dispersed in a thermoplastic matrix. The elastomers may optionally additionally contain conventional polymer additives such as processing aids, colorants, tackifiers, lubricants, silica, talc, or processing oils such as mineral oil in suitable amounts.

Suitable thermoset rubbers include butyl rubbers, chlorobutyl rubbers, bromo-butyl rubbers, nitrile rubbers, silicone rubbers, flurosilicone rubbers, fluorocarbon rubbers, polysulphide rubbers, polypropylene oxide rubbers, isoprene rubbers, isoprene-isobutene rubbers, isobutylene rubbers or neoprene (polychloroprene) rubbers.

Suitable thermoplastic elastomers comprise a copolymer of about 80 to about 95 mole percent ethylene and a total of about 5 to about 20 mole percent of one or more comonomers selected from the group consisting of 1-butene, 1-hexene, and 1-octene as known in the art. Two or more such copolymers may be blended together to form a thermoplastic polymer blend.

Another suitable class of thermoplastic elastomers are the styrene-ethylene/butylene-styrene block copolymers. These copolymers may additionally comprise a polyolefin (e.g. polypropylene) and a siloxane.

Thermoplastic elastomeric material may also be selected from one or more of the following: polyester rubbers, polyurethane rubbers, ethylene vinyl acetate rubber, styrene butadiene rubber, copolyether ester TPE, olefinic TPE, polyester amide TPE and polyether amide TPE.

Other suitable elastomers include ethylene propylene diene rubber (EPDM). The EPDM may be present on its own or present as part of a thermoplastic elastomer blend or alloy, e.g. in the form of particles substantially uniformly dispersed in a continuous thermoplastic matrix (e.g. polypropylene or polyethylene). Commercially available thermoplastic elastomer blend and alloys include the SANTOPRENE™ elastomers. Other suitable thermoplastic elastomer blends include butyl-polyethylene (e.g. in a ratio ranging between about 2:3 and about 3:2) and butyl-polypropylene.

Preferably the rigid component comprises at least 50% of the sealing ring and/or second sealing ring.

Preferably the sealing ring and/or second sealing ring is formable by a moulding process.

Preferably the moulding process is a two-stage injection moulding process. Preferably the two-stage injection moulding process is co-injection moulding.

Alternatively the moulding process is insert moulding.

Preferably the sealing ring and/or second sealing ring is not movable relative to the valve body. More preferably the sealing ring and/or second sealing is held within a cavity in the valve body.

Preferably, the stem comprises lubricant material. Suitably, the valve stem comprises up to 30%, preferably from 5 to 20% lubricant material.

Preferably, the sealing ring and/or second sealing ring comprise lubricant material. Suitably, the sealing ring and/or second sealing ring comprises up to 30%, preferably from 5 to 20% lubricant material.

Lubricant can be applied to the stem, sealing ring or second sealing ring by any suitable process including coating and impregnation, such as by injection or a tamponage process.

According to another aspect of the present invention, there is provided an aerosol container comprising a valve as described hereinabove.

Preferably, the aerosol container comprises a suspension of a medicament in a propellant. Preferably, the propellant is liquefied HFA134a or HFA-227 or mixtures thereof.

Preferably, the medicament is selected from albuterol, salmeterol, fluticasone propionate, beclomethasone dipropionate, ipratropium bromide and salts or solvates thereof and any combination thereof.

A particularly preferred combination comprises salmeterol xinafoate and fluticasone propionate.

BRIEF DESCRIPTION OF THE DRAWINGS

The invention will now be described further with reference to the accompanying drawing in which.

DETAILED DESCRIPTION OF THE DRAWINGS

Figure 1:
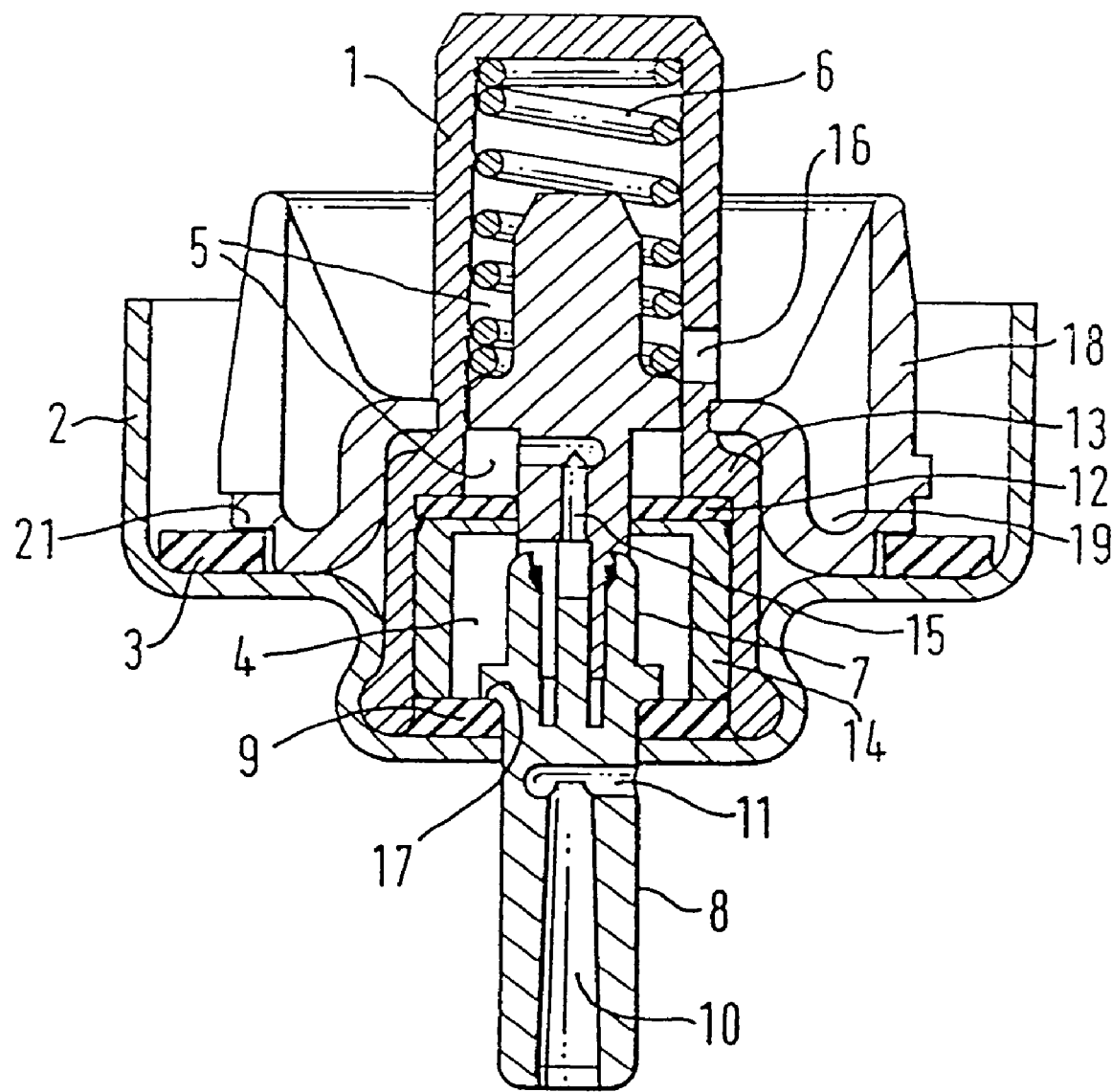
FIG. 1 is a section through a prior art metering valve.

A prior art metering valve is shown in FIG. 1 and comprises a valve body 1 sealed in a ferrule 2 by means of crimping, the ferrule itself being set on the neck of a container (not shown) with interposition of a gasket 3 in a well-known manner. The container is loadable with a suspension of medicament, such as salmeterol xinafoate in liquid propellant HFA134a.

The valve body 1 is formed at its lower part with a metering chamber 4, and its upper part with a sampling chamber 5 which also acts as a housing for a return spring 6. The words "upper" and "lower" are used for the container when it is in a use orientation with the neck of the container and valve at the lower end of the container which corresponds to the orientation of the valve as shown in FIG. 1. Inside the valve body 1 is disposed a valve stem 7, a part 8 of which extends outside the valve through lower stem seal 9 and ferrule 2. The stem part 8 is formed with an inner axial or longitudinal canal 10 opening at the outer end of the stem and in communication with a radial passage 11.

The upper portion of stem 7 has a diameter such that it can pass slidably through an opening in an upper stem seal 12 and will engage the periphery of that opening sufficiently to provide a seal. Upper stem seal 12 is held in position against a step 13 formed in the valve body 1 between the said lower and upper parts by a sleeve 14 which defines the metering chamber 4 between lower stem seal 9 and upper stem seal 12. The valve stem 7 has a passage 15 which, when the stem is in the inoperative position shown, provides a communication between the metering chamber 4 and sampling chamber 5, which itself communicates with the interior of the container via orifice 16 formed in the side of the valve body 1.

Valve stem 7 is biased downwardly to the inoperative position by return spring 6 and is provided with a shoulder 17 which abuts against lower stem seal 9. In the inoperative position as shown in FIG. 1 shoulder 17 abuts against lower stem seal 9 and radial passage 11 opens below lower stem seal 9 so that the metering chamber 4 is isolated from canal 10 and suspension inside cannot escape.

A ring 18 having a "U" shaped cross section extending in a radial direction is disposed around the valve body below orifice 16 so as to form a trough 19 around the valve body. As seen in FIG. 1 the ring is formed as a separate component having an inner annular contacting rim of a diameter suitable to provide a friction fit over the upper part of valve body 1, the ring seating against step 13 below the orifice 16. However, the ring 18 may alternatively be formed as an integrally moulded part of valve body 1.

To use the device the container is first shaken to homogenise the suspension within the container. The user then depresses the valve stem 7 against the force of the spring 6. When the valve stem is depressed both ends of the passage 15 come to lie on the side of upper stem seal 12 remote from the metering chamber 4. Thus a dose is metered within the metering chamber. Continued depression of the valve stem will move the radial passage 11 into the metering chamber 4 while the upper stem seal 12 seals against the valve stem body. Thus, the metered dose can exit through the radial passage 11 and the outlet canal 10.

Releasing the valve stem causes it to return to the illustrated position under the force of the spring 6. The passage 15 then once again provides communication between the metering chamber 4 and sampling chamber 5. Accordingly, at this stage liquid passes under pressure from the container through orifice 16, through the passage 15 and thence into the metering chamber 4 to fill it.

FIG. 1 illustrates a prior art valve with single component square cut valve seals, while the current invention describes the use of two component seals to reduce the 'notchiness' during actuation of the inhaler device. The two component valve seal, consisting of a rigid component and a flexible component, replaces the square cut single component seals shown in FIG. 1. The details of the arrangements of the two components of the sealing ring according to the invention are described below and illustrated in FIGS. 2a to 2l.

Figure 2A:
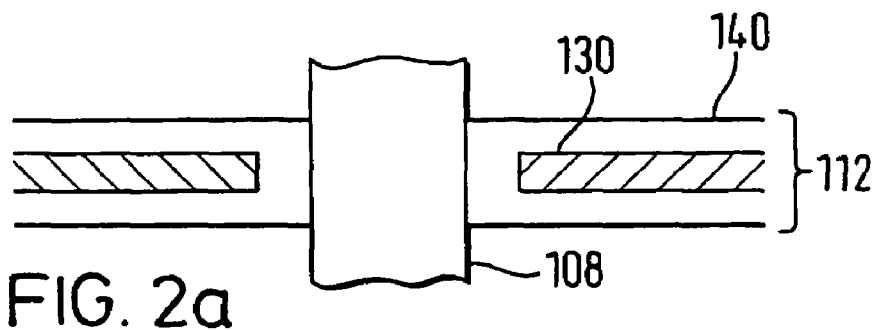
FIGS. 2a to 2l are close up sectional views of a seal-stem contact point in a valve, showing some different arrangements of the rigid and flexible components and the shape of the stem receiving part of the seal, according to the invention.

FIG. 2a shows upright valve stem 108, which has a circular cross-section. The valve stem 108 is sealingly contacted by a sealing ring 112. Sealing ring 112 has a rigid core 130 surrounded by flexible material 140.

Figure 2B:
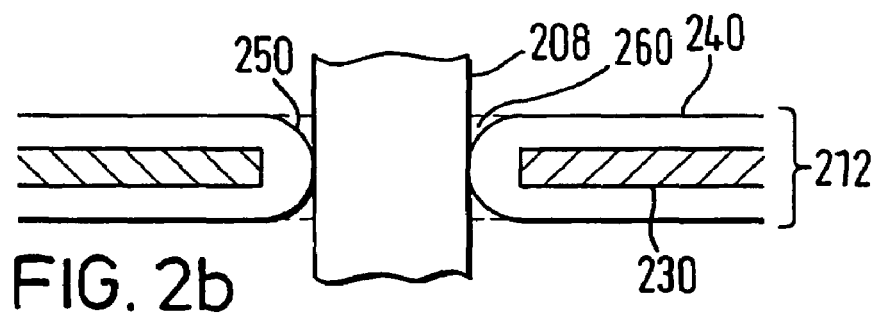

FIG. 2b shows upright valve stem 208, which has a circular cross-section. The valve stem 208 is sealingly contacted by a sealing ring 212. Sealing ring 212 has a rigid core 230 surrounded by flexible material 240. The ring aperture 250 of the sealing ring 212 has rounded edges. It may be understood that the area of contact of the ring 212 with the stem 208 is less than it would be if the ring 212 had square-cut edges. When the stem 208 is moved upwards, the ring 212 will tend to flex into free-space 260.

Figure 2C:
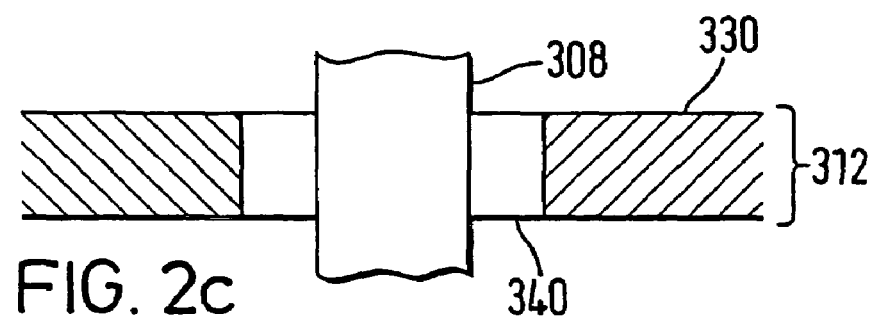

FIG. 2c shows upright valve stem 308, which has a circular cross-section. The valve stem 308 is sealingly contacted by a sealing ring 312. Sealing ring 312 has an outer rigid component 330 and a flexible inner component 340.

Figure 2D:
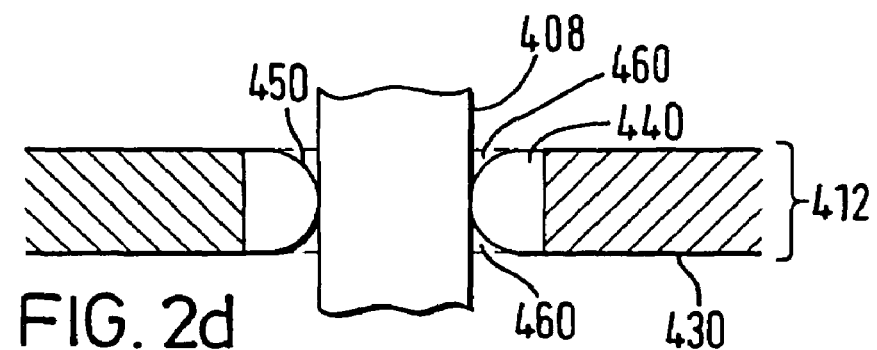

FIG. 2d shows upright valve stem 408, which has a circular cross-section. The valve stem 408 is sealingly contacted by a sealing ring 412. Sealing ring 412 has an outer rigid component 430 and a flexible inner component 440. The ring aperture 450 of the sealing ring 412 has rounded edges. It may be understood that the area of contact of the ring 412 with the stem 408 is less than it would be if the ring 412 had square-cut edges. When the stem 408 is moved upwards, the ring 412 will tend to flex into free-space 460.

Figure 2E:
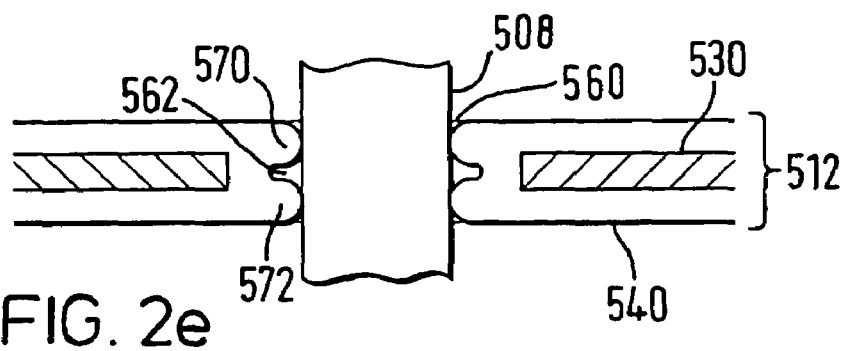

FIG. 2e shows upright valve stem 508, which has a circular cross-section. The valve stem 508 is sealingly contacted by a sealing ring 512. Sealing ring 512 has a rigid core 530 surrounded by flexible material 540. The ring aperture of the sealing ring 512 is edged by two rounded lobes 570, 572. The area of contact of the ring 512 with the stem 508 is less than it would be if the ring 512 had square-cut edges. When the stem 508 is moved within the ring 512, the ring 512 will tend to flex into free-space 560 and well 562. The well 562 may be wholly or partially filled with a lubricant material.

Figure 2F:
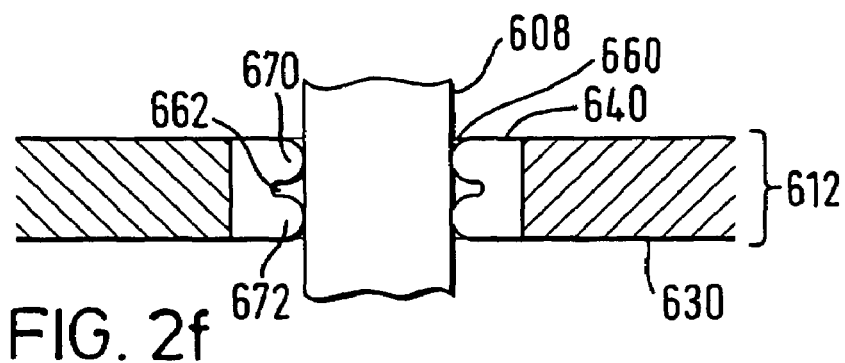

FIG. 2f shows upright valve stem 608, which has a circular cross-section. The valve stem 608 is sealingly contacted by a sealing ring 612. Sealing ring 612 has an outer rigid component 630 and a flexible inner component 640. The ring aperture of the sealing ring 612 is edged by two rounded lobes 670, 672. The area of contact of the ring 612 with the stem 608 is less than it would be if the ring 612 had square-cut edges. When the stem 608 is moved within the ring 612, the ring 612 will tend to flex into free-space 660 and well 662. The well 662 may be wholly or partially filled with a lubricant material.

Figure 2G:
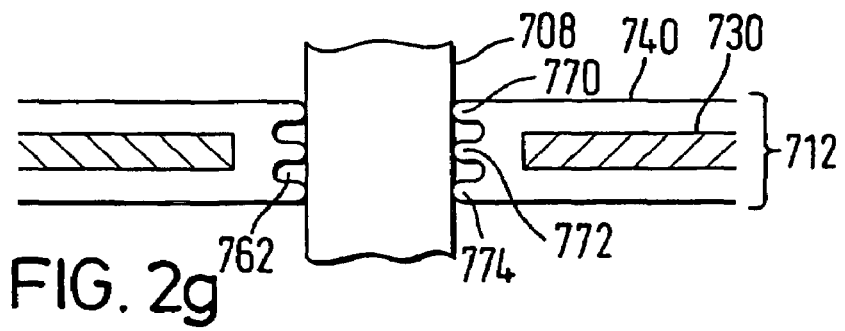

FIG. 2g shows upright valve stem 708 which has a circular cross-section. The valve stem 708 is sealingly contacted by a sealing ring 712. Sealing ring 712 has a rigid core 730 surrounded by flexible material 740. The ring aperture of the sealing ring 712 is edged by three rounded lobes 770, 772, 774. The area of contact of the sealing ring 712 with the stem 708 is less than it would be if the sealing ring 712 had square-cut edges. The areas defined by the stem and the lobes of the sealing ring define wells 762. These wells 762 may be wholly or partially filled with a lubricant material.

Figure 2H:
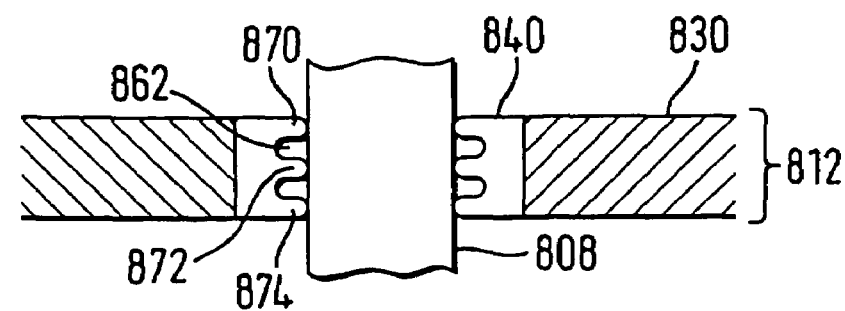

FIG. 2h shows upright valve stem 808 which has a circular cross-section. The valve stem 808 is sealingly contacted by a sealing ring 812. Sealing ring 812 has an outer rigid component 830 and a flexible inner component 840. The ring aperture of the sealing ring 812 is edged by three rounded lobes 870, 872, 874. The area of contact of the sealing ring 812 with the stem 808 is less than it would be if the sealing ring 812 had square-cut edges. The areas defined by the stem and the lobes of the sealing ring define wells 862. These wells 862 may be wholly or partially filled with a lubricant material.

Figure 2I:
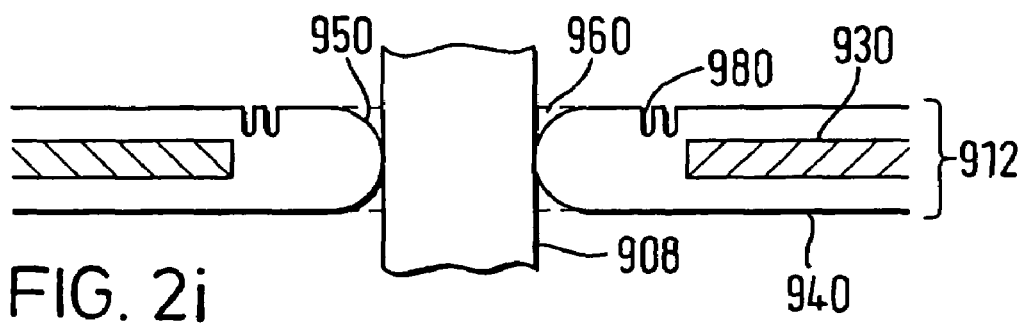

FIG. 2i shows upright valve stem 908, which has a circular cross-section. The valve stem 908 is sealingly contacted by a sealing ring 912. Sealing ring 912 has a rigid core 930 surrounded by flexible material 940. The ring aperture 950 of the sealing ring 912 has rounded edges. It may be understood that the area of contact of the ring 912 with the stem 908 is less than it would be if the ring 912 had square-cut edges. When the stem 908 is moved upwards, the ring 912 will tend to flex into free-space 960. The non stem-receiving part of the sealing ring 912 includes at least one groove 980 which provides additional free space for the sealing ring 912 to flex back into when the stem 908 is moved upwards.

Figure 2J:
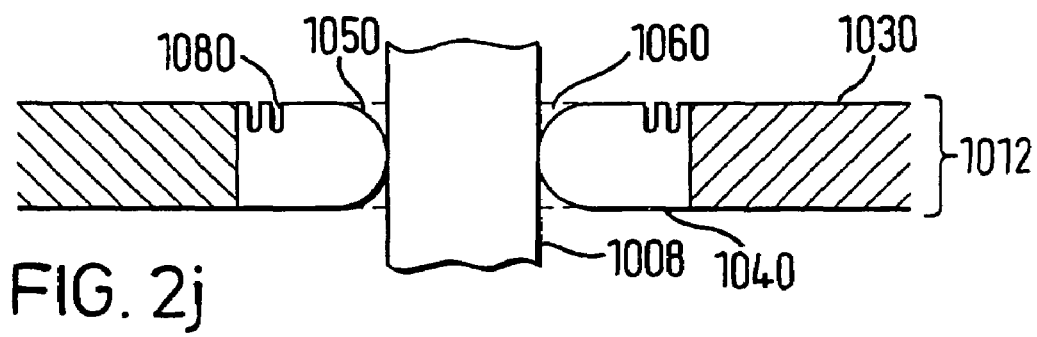

FIG. 2*j* shows upright valve stem 1008, which has a circular cross-section. The valve stem 1008 is sealingly contacted by a sealing ring 1012. Sealing ring 1012 has an outer rigid component 1030 and a flexible inner component 1040. The ring aperture 1050 of the sealing ring 1012 has rounded edges. It may be understood that the area of contact of the ring 1012 with the stem 1008 is less than it would be if the ring 1012 had square-cut edges. When the stem 1008 is moved upwards, the ring 1012 will tend to flex into free-space 1060. The non stem-receiving part of the sealing ring 1012 includes at least one groove 1080 which provides additional free space for the sealing ring 1012 to flex back into when the stem 1008 is moved upwards.

Figure 2K:
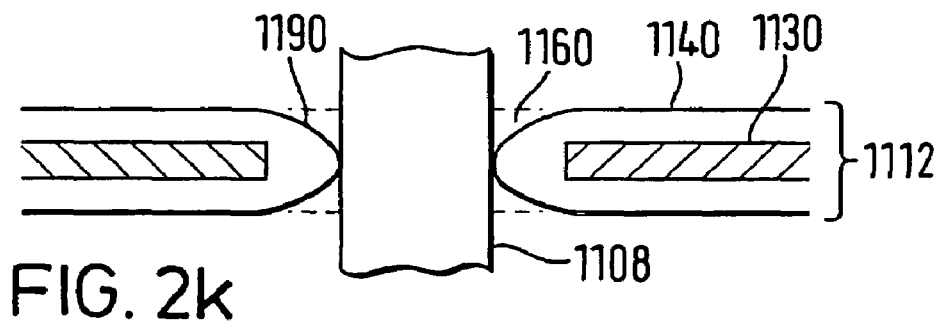

FIG. 2*k* shows upright valve stem 1108, which has a circular cross-section. The valve stem 1108 is sealingly contacted by a sealing ring 1112. Sealing ring 1112 has a rigid core 1130 surrounded by flexible material 1140.The ring aperture of the sealing ring 1112 has tapered edges 1190. It may be understood that the area of contact of the ring 1112 with the stem 1108 is less than it would be if the ring 1112 had square-cut edges. When the stem 1108 is moved upwards, the ring 1112 will tend to flex into free-space 1160.

Figure 2L:
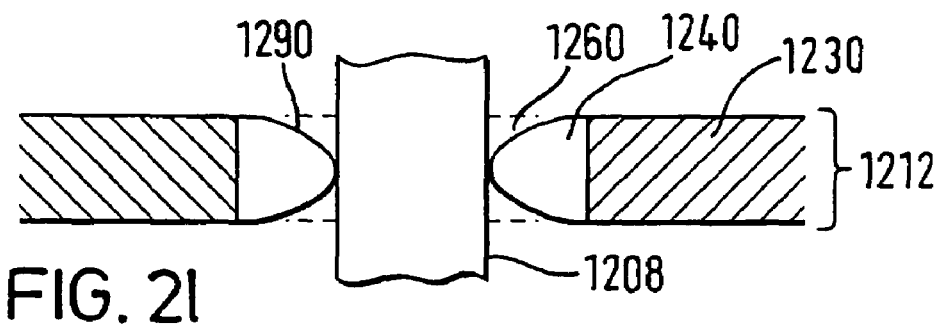

FIG. 2*l* shows upright valve stem 1208, which has a circular cross-section. The valve stem 1208 is sealingly contacted by a sealing ring 1212. Sealing ring 1212 has an outer rigid component 1230 and a flexible inner component 1240. The ring aperture 1290 of the sealing ring 1212 has tapered edges. It may be understood that the area of contact of the ring 1212 with the stem 1208 is less than it would be if the ring 1212 had square-cut edges. When the stem 1208 is moved upwards, the ring 1212 will tend to flex into free-space 1260.

The aerosol container and valve of the invention is suitable for dispensing medicament, particularly for the treatment of respiratory disorders. Medicaments which may be administered in the aerosol formulations include any drug useful in inhalation therapy. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. beclomethasone, flunisolide, budesonide, tipredane, triamcinolone acetonide, fluticasone or mometasone; antitussives, e.g. noscapine; bronchodilators, e.g. ephedrine, epinephrine, fenoterol, formoterol, isoprenaline, metaproterenol, phenylephrine, phenylpropanolamine, pirbuterol, reproterol, rimiterol, salbutamol, salmeterol, terbutaline, isoetharine, tulobuterol, 4-hydroxy-7-[2-[[2-[[3-(2-phenylethoxy)propyl]sulfonyl]ethyl]amino]ethyl-2(3H)-benzothiazolone; orciprenaline, or (−)-4-amino-3,4-dichloro-α-[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament and/or to minimize the solubility of the medicament in the propellant. It will further be clear to a person skilled in the art that where appropriate, the medicaments may be used in the form of a pure isomer, for example, R-salbutamol or RR formoterol.

Particularly preferred medicaments for administration using aerosol formulations in accordance with the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or the sulphate salt), salmeterol (e.g. as the xinafoate salt), formoterol (e.g. as the fumarate salt), terbutaline (e.g. as the sulphate salt), reproterol (e.g. as the hydrochloride salt),a beclomethasone ester (e.g. the dipropionate), a fluticasone ester (e.g. the propionate). Salmeterol, especially salmeterol xinafoate, salbutamol, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Aerosol compositions containing two active ingredients are known for the treatment of respiratory disorders such as asthma, for example, formoterol and budesonide, salmeterol (e.g. as the xinafoate salt) and fluticasone (e.g. as the propionate ester), salbutamol and beclomethasone (as the dipropionate ester) are preferred The term 'lubricant' herein means any material which reduces friction between the valve stem and seal or reduces the tendency of medicament to adhere to any parts of the metering valve which contact the medicament suspension. Suitable lubricants include fluoropolymers such as polytetrafluoroethylene (PTFE), fluoroethylene propylene (FEP), polyfluoro-cyclohexane, polyfluoro-hexane, trifluoroethylene, vinylidene fluoride and vinyl fluoride. Other suitable inorganic coatings which may be used to reduce adherence or which enhance the barrier properties to HFA134a, moisture, or drug absorption, include silicone oil or siloxanes such as dimethyl siloxane. Any movable parts may also have coatings applied thereto, which enhance their desired movement characteristics.

Frictional coatings may therefore be applied to enhance frictional contact and lubricants used to reduce frictional contact as necessary.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:
1. A valve comprising:
a body, a stem having a dispensing passage for dispensing a substance from the valve when the valve is open, and a one-piece sealing ring having an annular body comprising a rigid component and a flexible component, the body having an aperture passing therethrough, wherein the stem is slidably mounted in the aperture in the sealing ring for reciprocal movement relative to the sealing ring between a closed position, which closes the valve, and an open position, which opens the valve, wherein the flexible component provides at least an inner section of the sealing ring body which is contiguous with the aperture such that all of a boundary surface of the aperture is presented by the flexible component and the flexible component is positioned radially between the rigid component and the stem, and wherein the boundary surface of the sealing ring aperture is in constant sealing contact with the stem.

2. A valve according to claim 1, wherein the flexible component has a Shore hardness value of 45 to 80.

3. A valve according to claim 1, wherein the rigid component has a Shore hardness value of greater than 80.

4. A valve according to claim 1, wherein the rigid component has a greater resistance to an aerosol propellant and/or moisture than the flexible component.

5. A valve according to claim 1, wherein the rigid component includes a material selected from the group consisting of a polybutylteraphthlate, polyoxymethylene, metal and nylon.

6. A valve according to claim 1, wherein the flexible component includes an elastomer.

7. A valve according to claim 1, wherein the sealing ring is static relative to the valve body.

8. A valve according to claim 1, wherein the stem is slidably mounted for reciprocal movement, along an axis, wherein the boundary surface is axially-oriented and constantly sealingly engages an axially-oriented surface of the valve stem, and wherein the boundary surface is the only surface of the sealing ring in contact with the axially-oriented stem surface.

9. A valve according to claim 1, wherein the rigid component is wholly disposed in an outer section of the sealing ring which is radially spaced from the aperture by the inner section.

10. A valve according to claim 1, wherein the sealing ring consists of the flexible and rigid components.

11. A valve comprising:

a body, a stem having a dispensing passage, and a one-piece sealing ring including a rigid component and a flexible component, wherein the stem is slidably moveable relative to the sealing ring from a closed position to an open position, wherein a portion of the first flexible component is positioned radially between the rigid component and the stem, wherein the sealing ring is a first sealing ring and further including a second one-piece sealing ring, wherein the body defines a metering chamber and a sampling chamber, wherein, in the closed position, the dispensing passage is isolated from the metering chamber and the metering chamber is in communication with the sampling chamber via a transfer passage, wherein, in the open position, the dispensing passage is in communication with the metering chamber and the transfer passage is isolated from the metering chamber, and wherein the second sealing ring includes a rigid component and a flexible component.

* * * * *